US012337152B2

United States Patent
Steck et al.

(10) Patent No.: US 12,337,152 B2
(45) Date of Patent: Jun. 24, 2025

(54) CLICK EVENT IDENTIFICATION IN DELIVERY DEVICES

(71) Applicant: Ypsomed AG, Burgdorf (CH)

(72) Inventors: Jürg Steck, Kirchberg (CH); Andreas Schneider, Bern (CH); Simon Dähler, Kirchberg (CH); Jürg Hirschel, Bern (CH); Krista Kappeler, Bern (CH); Florian Kühni, Bern (CH); Simon Schüpbach, Bern (CH); Amir Feriani, Auvernier (CH); Ludovic Zulliger, Orbe (CH)

(73) Assignee: Ypsomed AG, Burgdorf (CH)

( * ) Notice: Subject to any disclaimer, the term of this patent is extended or adjusted under 35 U.S.C. 154(b) by 1125 days.

(21) Appl. No.: 16/950,113

(22) Filed: Nov. 17, 2020

(65) Prior Publication Data

US 2021/0085880 A1 Mar. 25, 2021

Related U.S. Application Data

(63) Continuation of application No. PCT/IB2019/053367, filed on Apr. 24, 2019.

(30) Foreign Application Priority Data

May 22, 2018 (EP) .................................... 18173675

(51) Int. Cl.
*A61M 5/315* (2006.01)
*G01C 19/00* (2013.01)
(Continued)

(52) U.S. Cl.
CPC ...... *A61M 5/31568* (2013.01); *A61M 5/3155* (2013.01); *A61M 5/3157* (2013.01);
(Continued)

(58) Field of Classification Search
None
See application file for complete search history.

(56) References Cited

U.S. PATENT DOCUMENTS 8,556,867 B2    10/2013   Price et al.
2011/0313395 A1*  12/2011  Krulevitch ........ A61M 5/31525
                                                            604/82
(Continued)

FOREIGN PATENT DOCUMENTS

EP       3381494 A1     10/2018
WO    2007107564 A1      9/2007
(Continued)

OTHER PUBLICATIONS

International Preliminary Report on Patentability received for International Application No. PCT/IB2019/053367 issued on Nov. 24, 2020, 9 pages.
(Continued)

*Primary Examiner* — Jenna Zhang
(74) *Attorney, Agent, or Firm* — Dorsey & Whitney LLP

(57) ABSTRACT

Monitoring an injection process executed by a variable dose injection device with feedback means for generating a number of feedback events proportionate to the dose to be determined is disclosed. A dialed or injected dose is determined by measuring a first signal of the process comprising a first signal peak related to a feedback event; detecting the first signal peak in the first signal; selecting an evaluation interval comprising the detected peak and adapted to an expected peak duration; deriving, from the first signal limited to the evaluation interval, a feature or characterizing parameter of the feedback event; identifying, from the derived feature, the feedback event as one of a dial up, dial down, or expel feedback event, and counting identified feedback events to determine the dialed or the ejected dose.

(Continued)

The two-stage approach with serially executed peak detection and peak identification allows to optimize data storage and processing power.

14 Claims, 5 Drawing Sheets

(51) Int. Cl.
- *G01P 15/18* (2013.01)
- *G16H 20/17* (2018.01)
- *G16H 40/40* (2018.01)
- *G16H 40/63* (2018.01)
- *G16H 40/67* (2018.01)
- *G16H 50/70* (2018.01)
- *A61M 5/31* (2006.01)

(52) U.S. Cl.
CPC ......... *A61M 5/31585* (2013.01); *G01C 19/00* (2013.01); *G01P 15/18* (2013.01); *G16H 20/17* (2018.01); *G16H 40/40* (2018.01); *G16H 40/63* (2018.01); *G16H 40/67* (2018.01); *G16H 50/70* (2018.01); *A61M 2005/3126* (2013.01); *A61M 2205/3327* (2013.01); *A61M 2205/52* (2013.01); *A61M 2205/581* (2013.01); *A61M 2205/582* (2013.01); *A61M 2205/8206* (2013.01)

(56) References Cited

U.S. PATENT DOCUMENTS

| | | | |
|---|---|---|---|
| 2012/0053527 A1* | 3/2012 | Cirillo | A61M 5/31525 604/189 |
| 2015/0206456 A1* | 7/2015 | Foster | G09B 23/30 434/262 |
| 2015/0246179 A1* | 9/2015 | Zur | G16H 40/67 604/207 |
| 2015/0290396 A1* | 10/2015 | Nagar | G16H 20/13 340/540 |
| 2016/0089154 A1* | 3/2016 | Chien | A61B 17/16 606/79 |
| 2016/0129182 A1* | 5/2016 | Schuster | A61M 15/008 702/56 |
| 2016/0213853 A1* | 7/2016 | Despa | A61M 5/31548 |
| 2016/0263327 A1* | 9/2016 | Radmer | G16H 20/10 |
| 2017/0182258 A1* | 6/2017 | Michael | G16H 20/17 |

FOREIGN PATENT DOCUMENTS

| | | |
|---|---|---|
| WO | 2014064691 A2 | 5/2014 |
| WO | 2015071354 A1 | 5/2015 |
| WO | 2016118736 A1 | 7/2016 |
| WO | 2018015401 A1 | 1/2018 |
| WO | 2018041798 A1 | 3/2018 |
| WO | 2019224626 A1 | 11/2019 |

OTHER PUBLICATIONS

Extended European Search Report received for European Patent Application No. 18173675.2, mailed on Oct. 29, 2018, 8 pages.
International Search Report and Written Opinion received for International Application No. PCT/IB2019/053367, mailed on Jul. 3, 2019, 12 pages.

* cited by examiner

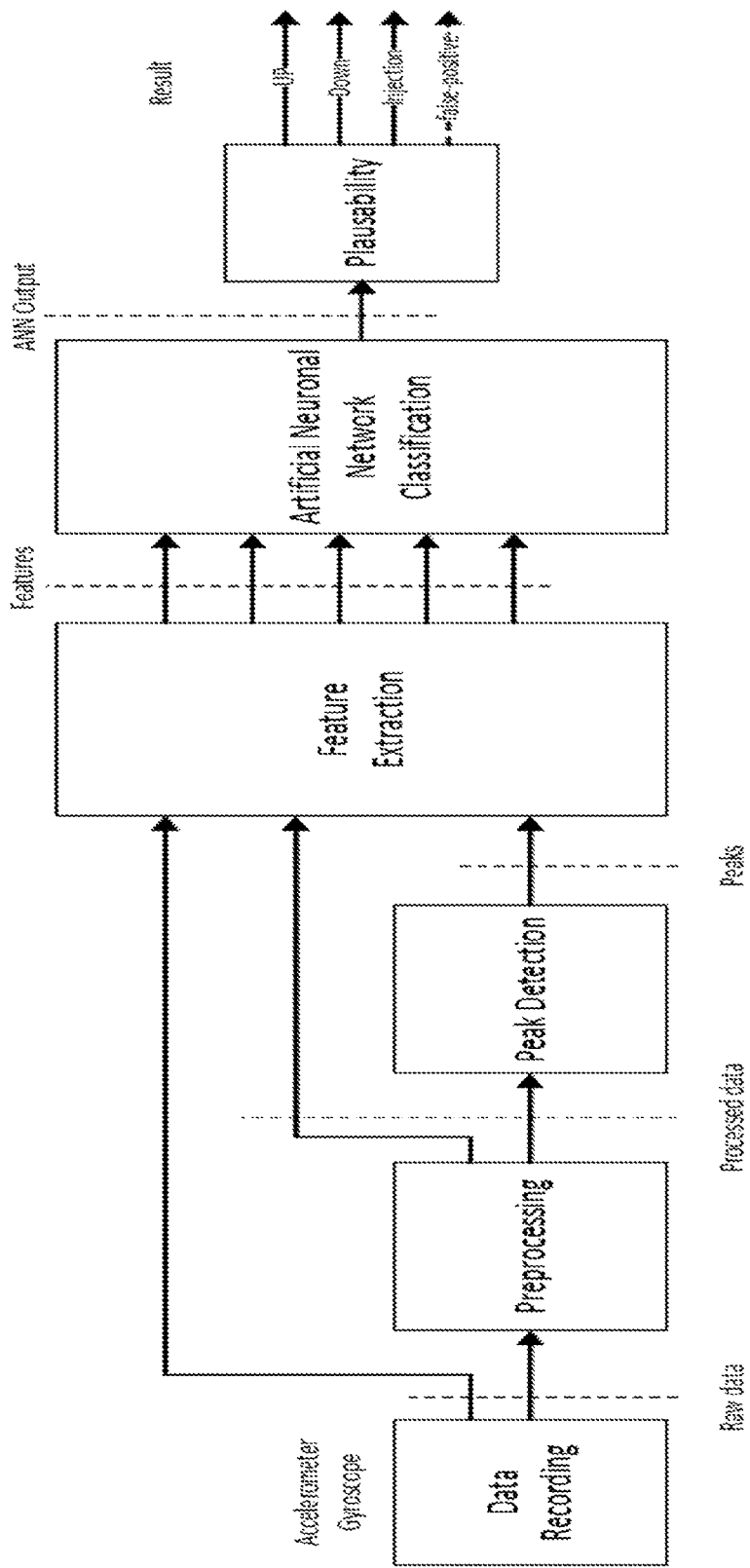

CLICK EVENT IDENTIFICATION IN DELIVERY DEVICES

This application claims priority to International Application No. PCT/IB2019/053367, filed Apr. 24, 2019, entitled "CLICK EVENT IDENTIFICATION IN DELIVERY DEVICES," which in turn claims priority to European Application No. 18173675.2, filed May 22, 2018, entitled "CLICK EVENT IDENTIFICATION IN DELIVERY DEVICES", each of which is incorporated by reference herein, in the entirety and for all purposes.

FIELD OF THE DISCLOSURE

The present disclosure relates to injection devices or medicament delivery devices for injecting, delivering, administering, infusing or dispensing substances and/or liquids such as insulin or hormone preparations. It begins from an electronic unit incorporated in, or attachable to, an injection device, and comprising a sensor unit for monitoring an injection process executed by means of the injection device.

BACKGROUND OF THE DISCLOSURE

A variety of diseases exist that require regular treatment by subcutaneous administration of a medicament, and a number of drug delivery devices have been developed to support a patient in accurately and controllably delivering an amount of drug in a self-administration process. Delivery devices include injection devices that are removed from the injection site after each medication event or drug delivery process, as well as infusion devices with a cannula or needle that remains in the skin of the patient for a prolonged period of time. Disposable delivery devices are adapted to deliver a drug from a container such as a pre-filled syringe that is not intended to be replaced or refilled by the patient. Reusable, semi-reusable, or hybrid delivery devices have a container that may be replaced by the patient, or a cartridge that may be refilled, while some components of the device may be reused with the replaced or refilled drug container.

By way of example, diabetes may be treated by self-administration of insulin with the help of multi-variable-dose insulin injection pens. An injection pen device generally has an elongate device body defining a longitudinal main device axis. The term "distal end" refers to the end of the injection device where an injection needle is located; the term "proximal end" designates the opposite end thereof. An automatic injection device has a motor or a drive spring for biasing a piston rod and shifting a piston in a container barrel, wherein the drive spring may have to be loaded or tensioned manually prior to injection of a dose. A manually powered delivery drive requires a user to manually provide the energy to move the piston, for instance by applying a distal force component to the injection device.

The insulin dose to be injected may typically be manually selected by turning a dosage knob and observing the actual dialed dose from a dose window or display of the insulin pen. A dose is dispensed by inserting the needle into a suitable portion of human skin and by moving the piston manually or by pressing a release button of an automatic injection device. In order to monitor the injection of insulin, for instance to prevent incorrect handling of the insulin pen or to keep track of the doses already applied, it is desirable to measure and process information related to a use of the injection device, such as information on the injected insulin type, dose, and circumstances of an injection process.

WO 2007/107564 proposes to record acoustic signals or vibration signals that may be associated with, in particular, a dose delivery of the medication or to a dose adjustment process. If a detected "click-sound" falls within a low frequency range, a unit dose of medicament is being set. Similarly, if the detected "click-sounds" fall within a high frequency range, a dose of medicament is being expelled from the medication delivery device. By counting the number of clicks during an expel sequence the amount of medicament expelled from the medicament delivery device can easily be calculated.

WO 2016/118736 discloses an injection device such as an insulin pen designed to produce an audible or tactile feedback to a user every time a dose unit is dialed or selected. Within the injection device, a sudden release of mechanical energy results in overall motion and vibrations transmitted through the injection device body or internal volumes of air, and manifests to the user through audible clicks and tactile feedback. Sensors are configured to detect such release of mechanical energy, and a microprocessor is configured to analyze data from the sensors to identify dose increasing dialing events and dose decreasing dialing events, and to distinguish dose dialing events from an accidental knock of the injection device or from an injection event. In specific embodiments, sensor data is collected at a 30 kHz sampling frequency from a single axis accelerometer, and repeatedly processed in overlapping data frames of less than 2 ms. A low frequency directional component of less than 100 Hz differs notably for increase and decrease dose dialing events, and a high frequency magnitude component including frequencies greater than 4 kHz represents a click sound.

US 2016/129182 proposes to compare a time waveform and/or frequency spectra of a vibration signal to pre-loaded analysis results related to previous or expected time waveforms and/or frequency spectra, to identify one of setting a desired dose or delivery of a set dose. Dose amounts are determined by counting vibrations associated with 1 IU or 0.5 IU of insulin. Vibration sensors respond to accelerations or velocities due to various types of oscillations, including shear, flexural, and surface oscillations. The vibration sensor may be an accelerometer comprising, for example, piezoelectric, piezo-resistive and/or capacitive components and/or may include a MEMS (Micro Electro-Mechanical System) device or component.

The above prior art approaches focus on a detection of a set dose or of an expelled dose in variable-dose injection devices by way of identifying and counting individual dosage units in a vibration pattern involving frequencies in the audible range and beyond. Reliably identifying individual clicks in a vibration signal as output by a conventional accelerometer requires the digital time-discrete accelerometer output signal to be available at an elevated resolution or sampling frequency. This in turn increases the requirements on data storage memory and processing power.

WO 2018/015401 discloses a device for generating protocol data for an injection pen, which is mounted to dosage adjusting means of the injection pen and/or to delivery means of the injection pen as an interface between a patient and the means. A patient adjusts the dosage of the medicament by rotating the device relative to the injection pen about an axis of rotation, and pushes the device towards the injection pen. The protocol data reflects an adjusted dosage of a medicament as well as an assumed delivery of the adjusted dosage of the medicament as inferred from a dosage-independent release or trigger activity of the user. A gyroscope signal indicative of a speed of rotation and acceleration of rotation of a selector dial coupled to a snap locking mechanism of the dosage adjusting means is used for peak detection. A data ring buffer provides data segments to an analyzer in accordance with the peak detection, which data segments include potentially relevant data related to the dosage adjusting means and/or to the delivery means. The analyzer implements a feature calculation for one or more components of the gyro signal, and the calculated features are classified in order to distinguish between dial up (dose setting) and dial-down (dose correction) peaks of the dosage adjustment activity.

In the present context, the terms "substance", "drug", "medicament" and "medication" are to be understood to include any flowable medical formulation suitable for controlled administration through a means such as, for example, a cannula or a hollow needle, and comprises a liquid, a solution, a gel or a fine suspension containing one or more medical active ingredients. A medicament can be a composition comprising a single active ingredient or a pre mixed or co-formulated composition with more than one active ingredient present in a single container. Medication includes drugs such as peptides (e.g., insulin, insulin-containing drugs, GLP-1 containing drugs or derived or analogous preparations), proteins and hormones, active ingredients derived from, or harvested by, biological sources, active ingredients based on hormones or genes, nutritional formulations, enzymes and other substances in both solid (suspended) or liquid form but also polysaccharides, vaccines, DNA, RNA, oligonucleotides, antibodies or parts of antibodies but also appropriate basic, auxiliary and carrier substances.

SUMMARY OF THE DISCLOSURE

It is an objective of the device to enable secure, easy and cost-effective operation of components, devices and systems for the generation, collection and distribution of data associated with the handling or use of injection devices. It is an objective of the device to monitor an injection process or medication event executed by means of a variable dose injection device, and specifically to determine the size of an adjusted or expelled dose, in a reliable manner. It is an objective of the described arrangement to identify the origin of a peak in a feedback signal of an injection device with reduced requirements on signal data memory space and processing power. These objectives are achieved by a method of determining a dose of a variable-dose delivery device and by an electronic module for a variable-dose delivery device according to the disclosure and claims. Various embodiments are evident from the disclosure and claims.

According to the disclosure, an expelled or a dialed dose is determined from feedback events of a variable-dose injection device having feedback means for generating a number of feedback events proportionate to the dose to be determined. The determination comprises the steps of
  measuring, during a dose expel or a dose setting process, by a first feedback sensor, a first signal of the process comprising a first signal peak related to a feedback event;
  optionally measuring, concurrently with the first signal, by a second feedback sensor, a second signal of the process comprising a second signal peak related to the feedback event;
  detecting, or localizing, the first signal peak in the first signal;
  selecting, or defining, an evaluation interval, or a region of interest, comprising the detected peak and adapted to an expected peak duration;
  deriving, from one of the first and the optional second signal limited to, or comprised within, the evaluation interval, a feature or characterizing parameter of the feedback event, or of the detected first or second signal peak related to the feedback event;
  identifying, from the derived feature, the feedback event, or the detected first or second signal peak related to the feedback event, as an expel feedback event generated by the feedback means during the dose expel process, or, in one variant, as one of a dial up or dial down feedback event generated by the feedback means during the dose setting process, and
  counting the number of identified feedback events to determine the expelled or the dialed (user set) dose.

The proposed two-stage approach with serially executed peak detection and peak identification separates an initial localization of a signal peak possibly related to a feedback event from a subsequent analysis of the detected signal peak in view of a possible source or origin feedback event. Contrary to a single stage approach that necessarily operates on the full, complete signal, the two stages may separately be optimized in view of data storage requirements and processing power. In particular, the limitation to an evaluation interval around a previously detected and confirmed peak entails a focus on the most significant data in the second stage and automatically discards peripheral data of lower relevance and avoids repeated processing of data samples in overlapping data frames. Dial-up, dial-down, and expel feedback events in injection devices with corresponding dial and expel feedback generation are distinguished and identified by a same set of signal evaluation steps, which further simplifies an implementation of the proposed approach. An expelled or ejected dose is determined by counting the number of expel feedback events rather than assuming the expelled dose to be equal to a previously adjusted dose, such that a separate expel trigger detection may be omitted in the proposed approach.

In a one variant of the device or method, the feature is derived from the second signal as limited to the evaluation interval, the boundaries of which in turn are defined by, or determined from, a peak locator of the detected first signal peak. In other words, the peak detection stage and the peak identification stage are executed on distinct signals representing distinct measurands or physical properties of the feedback event as measured by distinct sensors. Choosing a second signal distinct from the first signal increases the flexibility and allows to opt for the most promising features for the second stage, irrespective of any previous peak detection requirements or preferences.

The feedback sensors may be of any type susceptible of producing a useful signal related to dose proportional feedback events, including an inductive, capacitive, optical, or acoustic non-contact sensor placed at least in proximity to the feedback means. In one embodiment, the sensor is a mechanical sensor adapted to detect mechanical feedback events, including audible clicks and tactile vibration bursts. Suitable mechanical feedback sensors include an acceleration sensor, a gyroscope sensor, a piezoelectric contact microphone sensor, or a force or pressure transducer. In one embodiment, an accelerometer signal is employed as the first signal for peak localization, and a gyroscope signal is employed as the second signal for feature derivation and peak identification. The mechanical sensors are beneficially integrated in the delivery device, or part of an electronic module mounted to the delivery device in a manner sufficient to enable the characteristics of a mechanical feedback event to be conveyed to the electronic module.

The various measurands or process quantities that are represented by the measured signals all relate to an operation of feedback means of the injection device that produce a number of successive mechanical feedback events proportionate to a dose of drug. Specifically, a resilient element such as a dosing and/or expel click spring may be strained by a ratchet element with wedge shaped teeth sliding over a counterpart toothing structure, and upon relaxation accelerate the ratchet or counterpart structure to abut and produce a click sound or vibration burst as a single feedback event. Back-and-forth motion of the ratchet or counterpart structure, and corresponding generation of detectable oscillations, is repeated in proportion to the dose.

A gyroscope or gyroscopic sensor may be used as an orientation sensor to detect small vibrational and rotational movement of the injection device in a plane perpendicular to the direction of gravity, and thus produce an indication about an azimuth direction relative to a reference direction. In contrast thereto, an accelerometer which measures proper acceleration, which is the acceleration experienced relative to freefall and felt by people and objects, may only be used for orientation sensing relative to the direction of gravity. Reverting to a gyroscopic orientation sensor other than a conventional accelerometer is particularly helpful for injection devices with tactile feedback generating elements such as ratchets that rotate around a device axis and feature wedge shaped teeth which in turn do give rise to oscillating tangential force components.

In one variant, the method comprises the steps of defining, in a measured signal or corresponding data stream, consecutive non-overlapping data frames of pre-defined length. In case a detected signal peak in a first data frame is close to a frame border and the corresponding, selected evaluation interval extends beyond the first data frame into a second or subsequent data frame, signal data of the selected evaluation interval in the first data frame is prepended to the second data frame. The concatenated, complete signal data of, or in, the evaluation interval is processed in view of peak identification as part of, and along with, any evaluation interval of the second data frame.

In another variant, the method comprises the steps of deriving, from the first or the second signal limited to the evaluation interval comprising a detected signal peak, a non-event feature, and comparing the derived non-event feature to suitable thresholds. From the comparison, the signal may be identified as a false positive that is to be disregarded for dose determination. In other words, at least one non-event or negative feature different from the peak-origin-identification features is derived, and a signal in the evaluation interval around a previously detected peak may be identified as a false positive based on the non-event feature. The non-event feature defines a sufficient criteria for peak exclusion, even if the signal in the evaluation interval at the same time formally qualifies as a dial up, a dial down, or an expel click event. False positives or feedback event artifacts are generated from shocks or by violently shaking the delivery device and may be readily observed as peaks in an acceleration signal.

According to the disclosure, an electronic module or auxiliary device for removable attachment to, and for monitoring an injection process performed by means of, a variable dose injection device comprises a first and optionally a second feedback sensor. The sensors are adapted to measure a first and second signal of a first and second process quantity of a dose setting or dose expel process of the delivery device. The respective signals comprise a first and second signal peak related to a feedback event generated by a feedback means of the variable dose delivery device, wherein the feedback means or signal source(s) generate a number of mechanical feedback events proportionate to a dose of drug to be determined. The electronic module comprises a processing unit connected to the sensor(s), and configured or programmed to perform the following steps: (i) detect, or localize, the first signal peak in the first signal; (ii) select, or define, an evaluation interval, or a region of interest, comprising the detected peak and adapted to an expected peak duration; (iii) derive, from one of the first and an optional second signal limited to, or comprised within, the evaluation interval, a feature or characterizing parameter of the feedback event, or of the detected first or second signal peak related to the feedback event, and (iv) identify, from the derived feature, the feedback event, or the detected first or second signal peak related to the feedback event, as one of a dial up, dial down, or expel feedback event. Optionally, the processing unit is further adapted to count the number of identified feedback events to determine the expelled or the dialed dose. For the purpose of the identification step, the processing unit may include a Neural Network based classifier operating on the feature values or feature instances calculated in the derivation step. Alternatively, the above-mentioned components of the electronic module may be included in an electronic unit that is a part of, or non-detachably embedded in, the delivery device.

In a further variant, the electronic module is adapted to be releasably attached, or detachably mounted, to a main housing or body of the injection device, which main housing is intended to be gripped by the user in a way such that tactile feedback generated by the feedback means or tactile source is readily perceivable by the user, in particular during injection. The electronic module includes attachment means for securing or even locking the module to the device housing, such as resilient wings embracing the device housing or biased protrusions engaging with counterpart recesses of the device housing. The electronic module may also include an elongate module housing with a handle or gripping part in turn adapted to be grasped by the user. In other words, the electronic module is not mounted to a dose dialing or injection triggering part of the injection device, and not intended to be rotated or otherwise moved by the user relative to the main housing. The electronic module is attached to the device housing in a sufficiently rigid manner to enable the mechanical feedback events to be conveyed or transmitted to the electronic module and to the feedback sensors without excessive attenuation or distortion.

In another variant, the electronic module comprises a printed circuit board and a planar battery with a main surface or battery plane. The processing unit and a feedback sensor are mounted on either side of the printed circuit board, and the battery is sized to power the electronic module. The battery is arranged with the main surface parallel to the board in a recess of the board and extending to a comparable extent to both sides of the board in a direction perpendicular to the plane, which results in a volume-saving arrangement of the module components.

In another variant, the electronic module comprises a module housing with an opening allowing a user to read a dose dialed and depicted in a window of the delivery device to which the electronic module is attached. A border, edge, or circumference of the opening surrounds the window and is illuminated to function as a status indicator, with different colors and illuminating schemes available to code distinct delivery status. The module housing to this purpose includes a light-guide sourced from an LED on the printed circuit board.

In still another embodiment the electronic module comprises an accelerometer and/or a gyroscope as a feedback sensor for dose detection. The signal processing unit is adapted to detect device handling activities by the user from a non-click sensor signal measured independent of a dose setting or dose expel process of the delivery device, and not related to a feedback event generated by feedback means internal to the delivery device. Device handling activities relate to movements of the delivery device and/or the electronic module as a whole, and include, for instance, attachment/removal of the module to/from the delivery device by way of a snap or clip operation; grasping of delivery device and attached module after having rested immobile for some time, device cap attachment/removal to/from the delivery device, cannula attachment or removal, near-vertical orientation of the delivery device during priming. Detection of the aforementioned user activities may advantageously be used, individually or in combination, as a basis for a plausibility check confirming or questioning an expected handling sequence. Upon detection of these activities, the electronic module may end a sleep or low-power mode and enter an injection monitoring mode. Likewise, a dedicated wake-up activity such as double tapping or knocking the device to end a sleep mode may be detected by the same feedback sensor that primarily serves for dose determination. In these cases, no button or switch may be needed on the electronic module to activate the electronic module.

In a specific variant of the preferred embodiment the feedback sensor is adapted to measure, during or in parallel to an expel process as delimited by Start/End-of-Injection clicks or by a first and a last dose unit expel click, a non-click sensor signal. The signal processing unit is configured to determine and track therefrom a relative position of the accelerometer and/or a gyroscope of the electronic module attached to, or integrated into, the delivery device. If the relative position, during the expel process, remains constrained in-between two concentric spherical surfaces of a radial distance not exceeding a maximum penetration depth of the delivery device, the expel process is acknowledged as an injection process. In other words, if the tracked position is not bound by the two spherical surfaces, the delivery device may not be assumed to have been in permanent contact with an injection site, implying that at least a part of the dose was not injected into a target tissue but rather ejected into the air. The tracked excursion of the delivery device during an expel process may thus serve as a basis for a plausibility check confirming, or even as a necessary condition for acknowledging, a successful delivery of a dose into the injection site.

In this context, the referenced distance between the two spherical surfaces is intended to reflect a maximum radial distance from an injection site that any point of the delivery device may travel without the tip of the cannula being retracted from the skin of the patient. Accordingly, the referenced distance may include, in addition to the penetration depth corresponding to the length of a distal part of the cannula protruding outside the delivery device, a maximum compression distance of the tissue at the injection site in a direction perpendicular to the surface. This implies that a cannula that has been inserted with maximum force may be retracted by a distance accounting for both initial tissue compression and penetration depth without leaving the skin. In practice, said radial distance may therefore amount to a few millimeters up to one centimeter. The proposed criteria for a restricted motion of the delivery device during injection distinguishes advantageously from prior art methods identifying injections coarsely from a pen being oriented essentially vertical.

Relative position changes of the feedback sensor may exemplarily be determined by integrating the measured instantaneous three-axis acceleration signals as provided by the accelerometer, and possibly eliminating the contribution of gravity by way of sensor fusion including corresponding gyroscope signals. Four consecutive position values separated by small time intervals allow to determine a radius of a spherical surface defined by the former. The size of the radius may be compared to a known distance between the feedback sensor and the tip of the injection device as the presumed center of the spherical surface, or the evolution of the radius over time may confirm or question consistency with the proposed criteria. In one variant, instead of determining position changes, the radial acceleration along a main axis of the delivery device is measured and checked for consistency with a centrifugal acceleration inferred from the tangential velocity in a plane perpendicular to the main axis as obtained by integration of the measured tangential acceleration. The determination of the centrifugal acceleration involves the distance between the feedback sensor and the tip of the injection device as the presumed radius of a pure spherical movement. A discrepancy between the measured radial acceleration and the inferred centrifugal acceleration will be indicative of an instantaneous radius different from said distance, which likewise questions injection into an intended injection site. In any case, it may be beneficial to place the acceleration and gyroscope sensors at or close to the proximal end of the delivery device, to optimize the non-radial acceleration components to be measured.

Further, the electronic module is devoid of any kind of additional optical, magnetic, electrical, or mechanical sensor and corresponding evaluation means for separately determining a dial direction of a dose dialing component of the delivery device, and the method of determining a dose does not rely on a separate binary signal indicative of the dose being increased or decreased and resulting from such an additional sensor different from the feedback sensor. Preferably, the electronic module is devoid of any kind of additional optical, magnetic, electrical, or mechanical sensor and corresponding evaluation means for separately determining a rotation or translation operation of an injection triggering component, and the method of determining a dose does not rely on a separate binary signal indicative of the dose being expelled, and resulting from such an additional sensor different from the feedback sensor.

The proposed two-stage approach with serially executed signal peak detection and signal peak identification is independent of the type of feedback event or feedback source to be identified. In particular, the device may likewise be beneficial to distinguish, in addition or alternatively, other feedback events than the dose unit dial events. For instance, Start-of-Injection (SoI) and/or End-of-Injection (EoI) feedback events may be generated by a delivery device and captured by appropriate feedback sensors, such that corresponding sensor signals may be analyzed in view of a distinction of potential source events.

In particular, the device may also benefit fixed-dose disposable injection devices including single-dose injection devices such as auto-injectors or patch injectors as well as multi-dose injection devices such as fixed dose injectors. Auto-injectors automatically eject a fixed dose of liquid drug from a pre-filled syringe by means of a pre-tensioned injection spring biasing a piston rod and shifting a piston in a syringe barrel. Fixed-dose injectors have a single, non-variable dosage volume, or may provide a limited number of fixed, non-variable injection dosage volumes for the user to choose from. Fixed-dose injection devices are devoid of dose unit feedback generation means, but provided with SoI and EoI feedback means producing suitable optical, acoustical or tactile user feedback.

Accordingly, the device and method may be directed to an electronic module for a fixed-dose delivery device comprising (a) a first feedback sensor adapted to measure a first signal comprising a first signal peak related to a feedback event generated by a feedback means of the delivery device, (b) optionally, a second feedback sensor adapted to measure a second signal comprising a second signal peak related to the feedback event, and (c) a processing unit. The latter is configured to (i) detect the first signal peak in the first signal, (ii) select an evaluation interval comprising the detected peak; (iii) derive, from one of the first and the optional second signal limited to the evaluation interval, a feature of the feedback event, and (iv) identify, from the derived feature, the feedback event as a Start-of-Injection click or as an End-of-Injection click.

Many of the variants noted previously in the context of a variable-dose delivery device also apply in the context of fixed-dose injection devices. Specifically, at least the steps of deriving the feature from the second signal; employing suitable mechanical feedback sensors including one of an acceleration sensor, a gyroscope sensor, a piezoelectric contact microphone sensor; defining successive data frames of pre-defined length; deriving a non-event feature to identify the signal as a false positive; and detecting device handling activities by the user from a non-click sensor signal captured independent of a feedback event, specifically tracking a position of the delivery device during an expel process, are seamlessly combinable with the aforementioned Start/End-of-Injection click identification in fixed-dose delivery devices.

BRIEF DESCRIPTION OF THE DRAWINGS

The subject-matter of the device and method will be explained in more detail in the65 following text with reference to exemplary embodiments as illustrated in the attached drawings, of which

FIG. 9 is a block diagram of an exemplary method of click event identification.

For consistency, the same reference numerals are used to denote similar elements illustrated throughout the drawings.

DETAILED DESCRIPTION OF PREFERRED EMBODIMENTS

Figure 1:
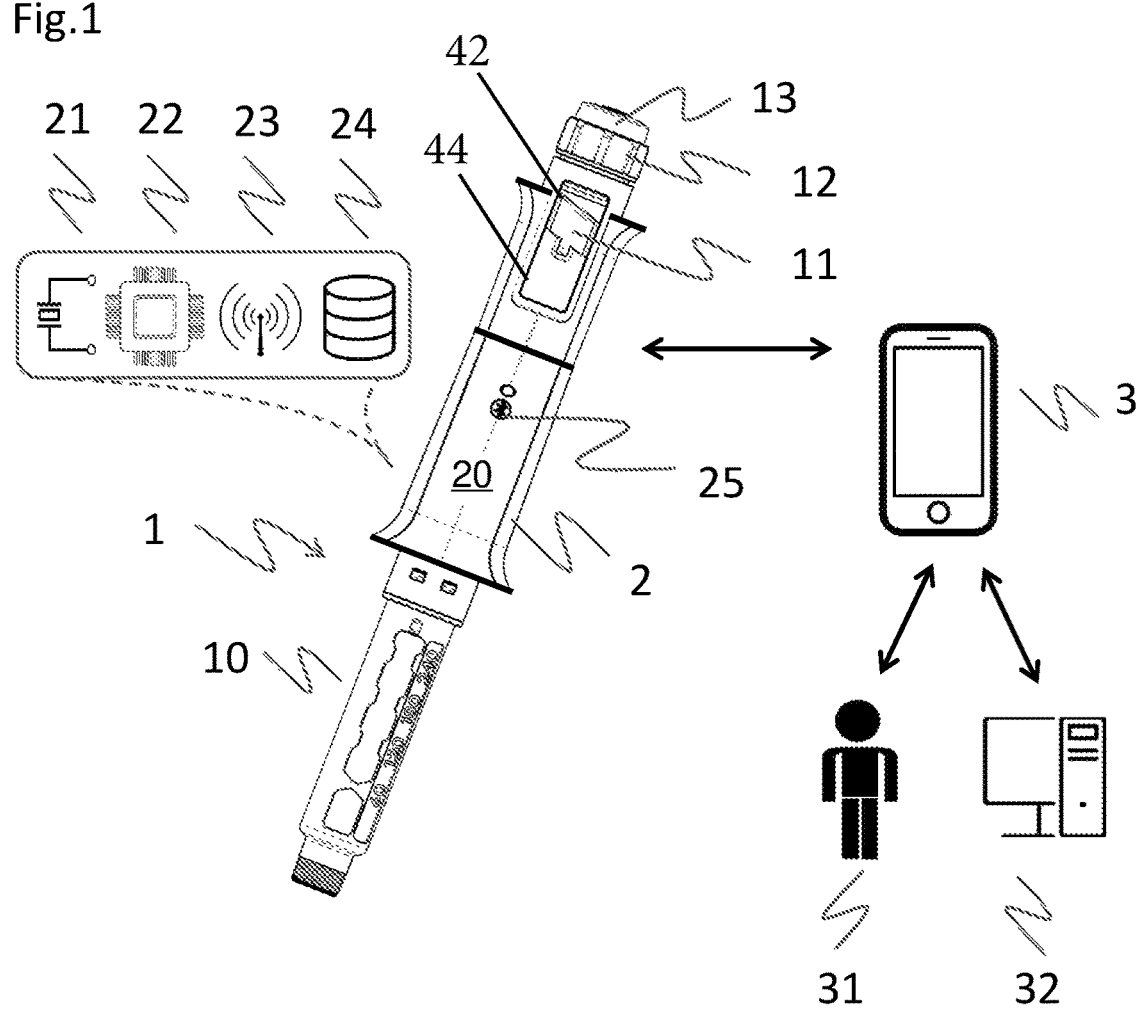
FIG. 1 depicts a medical injection monitoring and patient support system.

FIG. 1 depicts a medical injection or drug delivery monitoring and patient support system, comprising a variable dose injection device 1, an electronic module 2 detachably mounted, or releasably attached, to the injection device, and a mobile device 3 (e.g., a telephone or tablet). The injection device includes an elongate device housing 10 essentially symmetric around a main device axis, as well as a dose dialing facility as amply described for instance in EP 2812055 and in turn including a dosing sleeve 11, a rotary dosing knob 12, and a discharge button 13. The dosing knob 12 enables the user to adjust a dose and is arranged on a proximal end of the dosing sleeve. The dosing sleeve 11 features markings in the form of numbers on its outer surface. When the dosing sleeve is screwed out of the housing 10 during the dosing operation, the adjusted dose is displayed in a window 42 of the housing. The discharge button 13 is snapped on the dosing sleeve 11 in such a way that the discharge button can slightly move axially relative to the dosing sleeve.

The electronic module 2 comprises an essentially tubular module housing surrounding the injection device 10 housing in the attached state, feedback sensor(s) 21, a processing unit 22 and a transmitter unit 23 for wireless transmission of data about the injection progress via Bluetooth Low Energy (BLE) or equivalent short or near range wireless communication technology to the mobile device 3. The electronic module 2 additionally includes a data storage unit 24 or memory connected to the processing unit 22 and a lock/release mechanism to secure the attachment of the electronic module 2 to the injection device. Connection and system status indicator 25 provides visual feedback about a connection status indicative of an established communication link to the mobile device 3, and about a device, module, or process status, including for instance an availability of battery power, a readiness of communication means, an attached/detached status of the electronic module 2 and the injection device 10, or a progress of an ongoing injection process. The electronic module 2 is further adapted to produce a time-stamp indicating at what date and time a monitored dose has been injected, and to store at least the dose expelled and the time-stamp in the data storage unit 24 for later upload.

The mobile device 3 is a smartphone or tablet device running a dedicated application program; or a laptop computer configured accordingly. The mobile device is adapted to interact with a respective patient 31 as well as a remote server, cloud based computing facility, or expert system 32. The mobile device 3 may comprise a bolus calculator for calculating insulin delivery doses, or be knowledgeable (via stored data) of a therapy plan, e.g., of a growth hormone therapy. Instantaneous bolus dose values or currently scheduled therapy dose values may be provided to the electronic module 2. Dialed doses are then monitored in real time and compared to the dose values due, and a discrepancy is signaled to the user, e.g., via indicator 25.

Turning the dosing knob 12 in a dose-increasing dialing direction or in a dose-reducing corrective direction causes a ratchet toothing to slide over a counterface toothing and to repeatedly perform a slight axial back and forth motion that gives rise to a clicking sound. The number of clicks is proportional to the dosage volume, wherein in one embodiment each click or vibration burst corresponds to a single dosage unit, such as an International Unit IU. During dose-discharge, a tooth of a flexible arm rotates relative to a grating, which in turn generates an acoustic click sound and a tactile discharge feedback signal to the user. The dialing, corrective, and discharge clicks are captured by the feedback sensors 21 and converted into a feedback signal on behalf of the processing unit 22.

The module housing 20 is designed to be positioned on the injection device housing in such a way as to neither interfere with the dial-and-dose components nor obscure any display window 42 or visual indicator of the device 1. To this purpose, the module housing has a recess or opening 44 that matches with the device window 42. Hence the patient may continue using a non-modified injection device in a known manner, despite the presence of the electronic module, with all device interface elements remaining fully accessible throughout the handling sequence. Specifically, in this case the electronic module 2 excludes the presence of a mechanical sensor to mechanically detect a rotation angle or linear shift of the dosing knob 12. Likewise, the electronic module 2 excludes the presence of an optical sensor to read a dialed dose from a dialing sleeve.

Figure 2:
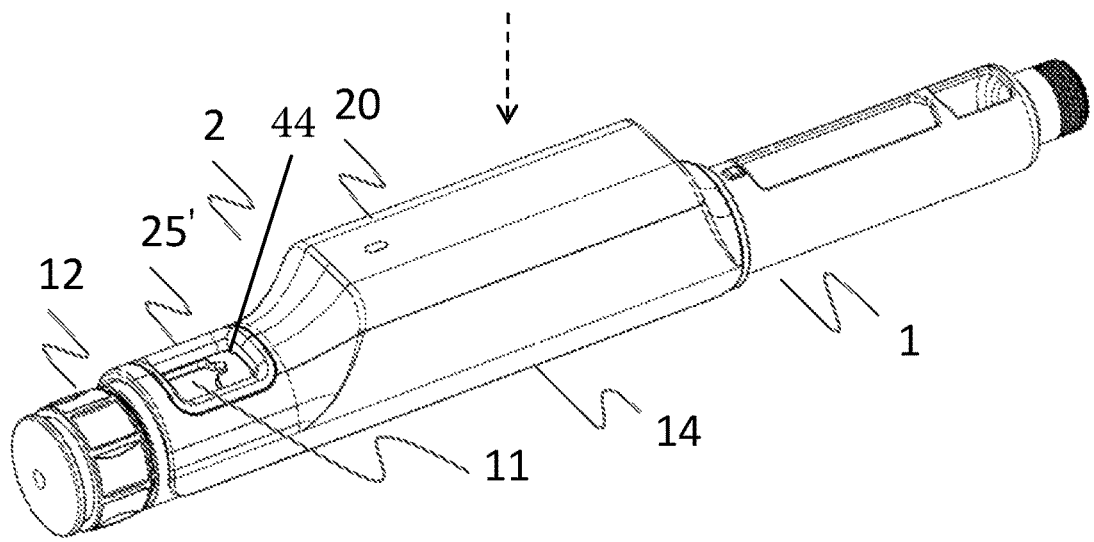
FIG. 2 shows an electronic module laterally attached to an injection device.

FIG. 2 depicts a differently-shaped electronic module 2 which is laterally attached to the injection device 1 by attachment means, such as a snap-fit or clip connection involving resilient module wings 14 on opposite sides of the device housing. The module housing 20 shown is not rotationally symmetrical such as the one in FIG. 1, but features a prominent laterally extending volume for accommodating the electronic components. The status indicator 25' is a light guide that surrounds or frames the rectangular opening 44 of the module 2 and the viewing window 42 of the device.

In preferred variants, the module or delivery status indicator 25, 25' serves to intuitively guide or at least support the patient through the delivery process. To that end, the status indicator 25, 25' emits a pulse of white light when the module is activated, at every dialed dosage unit or identified click event, at the start or end of dose ejection, and/or at the beginning of the holding time. Instead of a single pulse, prolonged pulses may be emitted continually and separated by shorter idle periods of no light emission. When a dialed or selected dose equals a previously established target dose, or when a delivery process has been successfully completed, this is indicated to the user by the status indicator 25, 25' being illuminated in continuous green light. On the other hand, the light of the indicator 25, 25' changes to blinking red if and as long as the correct dose has been exceeded, or in other error cases, including an insufficient holding time or a premature lift-off as determined from a feedback sensor signal after completion of the fluid ejection. Reverting to distinct signaling modes (continual, continuous, and blinking) in addition to color coding also enables color-blind users to take full advantage of the monitoring capabilities of the electronic module.

Figure 3A:
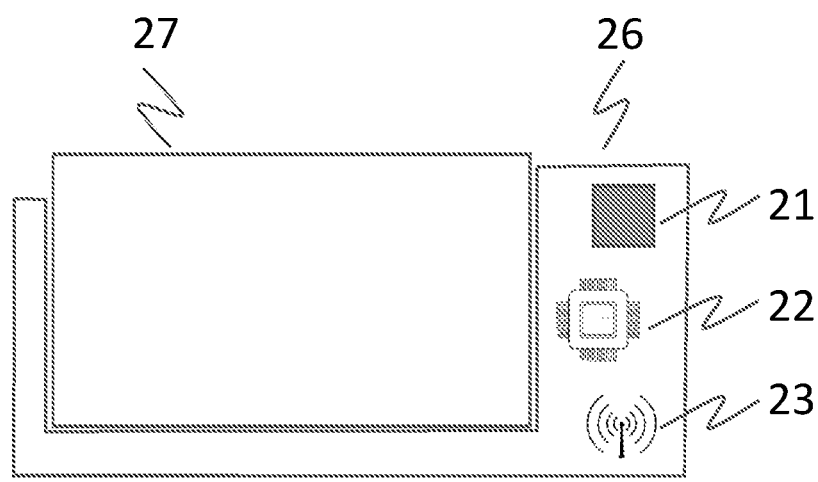
FIGS. 3A and 3B schematically depict a top and front view, respectively, of some module components as arranged in the electronic module of FIG. 2.
Figure 3B:
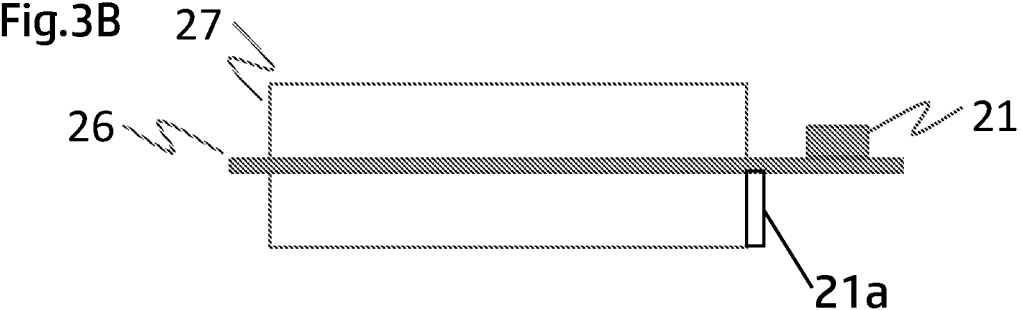

FIG. 3A schematically depicts a top view and FIG. 3B a front view of some of the components of the electronic module of FIG. 2, wherein the top view is in a direction perpendicular to a main device axis as indicated by the broken-line arrow in FIG. 2. The prominent laterally extending part of the module housing 20 holds a Printed Circuit Board (PCB) 26 onto which are mounted an Inertia Measurement Unit (IMU) as a first feedback sensor 21, connected with a microcontroller chip as the processing unit 22, as well as a Bluetooth Low Energy (BLE) chip and antenna as the transmitter unit 23. Furthermore, a micro-USB connector may be provided, as well as, on a device-facing side of the PCB, a mechanical contact switch for detecting attachment of the electronic module to the delivery device, or a sensor such as a piezo contact microphone likewise contacting the delivery device housing in the attached state and acting as a second feedback sensor 21*a*. LEDs are provided on the PCB to illuminate the status indicator 25 via light guides or optical light piping. Alternatively, and in order to avoid excessive attenuation of the status indicator light in the light guides, the LEDs may be mounted onto an additional, flexible PCB provided closer to the location of the status indicator 25' in the module housing 20. The IMU 21 may be a six axis IMU integrating both a three-axis accelerometer and a three-axis gyroscope as distinct feedback sensors in the context of the present disclosure.

The aforementioned components of the electronic module are sourced from a battery 27, preferably a rechargeable Lithium Polymer (LiPo) battery that may be recharged via the micro-USB connector. The battery 27 has a flat body with a rectangular planar main surface and a height or vertical extension in a direction perpendicular to the main surface. The PCB 26 is adapted for accommodating the battery 27 with the main surface parallel to the PCB plane in a rectangular recess or bay with a linear dimension slightly exceeding a length of the surface of the battery. The accommodated battery 27 extends vertically to both sides of the PCB, in particular to a same extent when mounted such that the PCB 26 at least partly surrounds the battery at about half height. In the attached state of the electronic module 2, the PCB 26 is arranged parallel to a main device axis, or tangential to a device surface. In an alternative variant, the battery 27 has a cylindrical body and is arranged on a device-facing side of the PCB with the cylinder axis parallel to the main axis of the device. Specifically, the cylindrical battery 27 may be accommodated in a space with triangular cross-section delimited by the device-facing side of the PCB 26, the circular outer surface of the device housing, and the inner side of the lateral module housing 20 part that seamlessly transitions into the resilient module wings 14.

The two-stage peak detection and peak identification strategy is executed continually on suitably defined data frames. At the processing unit 22, sensor data is made available the peak detection stage and to the peak identification stage (each of which may comprise stored computer programs or signal-processing circuits) in the form of data frames or data packets. A convenient frame length or size may be chosen between 2 and 200 ms, in one embodiment between 10 and 100 ms, and in another embodiment between 20 and 50 ms. A typical data frame has a length of about 40 ms which corresponds to no less than 400 samples at a sampling frequency of 10 kHz or 160 samples at a sampling frequency of 4 kHz. In any case the frame length is more than the time needed to execute the aforementioned functions and short enough to not induce a perceptible delay at the mobile device 3 of the user. For suspected and/or detected peaks that accidentally appear at or close to a boundary of a data frame some localization and/or identification-relevant data may be lost. Therefore, incomplete peak localization and/or identification data at the end of a data frame is prepended to the next data frame in order to ensure that a full evaluation interval 40 as detailed below is available to localize and/or identify the border peak. Such localization and/or identification takes place together with the localization and/or identification of all further peaks of the next data frame that may in turn be assigned a complete evaluation interval.

The peak detection or peak localization may be performed according to a suitable algorithm frame by frame on a stream of first-signal data frames. In a preferred embodiment, acceleration (XL) data from a multiple axis accelerometer is evaluated. In an initial pre-processing step, the acceleration components along three mutually orthogonal x, y, z axis are passed through a high-pass digital Finite Impulse Response FIR filter. A magnitude of the acceleration $XL_{mag}$ is then calculated from the three filtered acceleration components $XL_x$, $XL_y$, $XL_z$ as:

$$XL_{mag} = \sqrt{(XL_x^2 + XL_y^2 + XL_z^2)}$$

It is apparent to the skilled person that characteristic signals other than the acceleration magnitude $XLma_g$ may be derived and used for peak detection, and that the filters described may be adapted or replaced.

Figure 4:
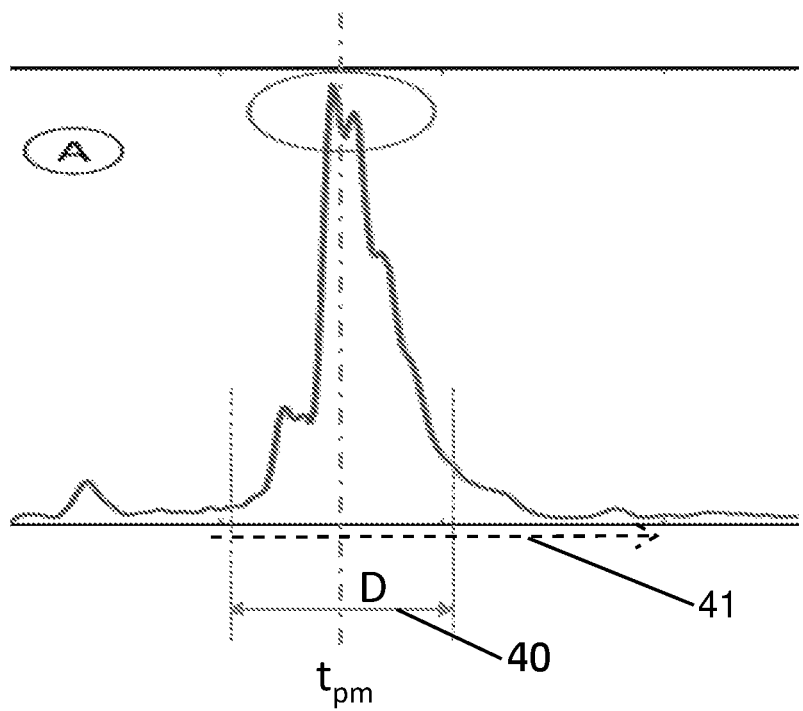
FIG. 4 shows a double peak in a signal related to a feedback event.

FIG. 4 shows a double peak found in the acceleration magnitude signal of a single ratchet click of a variable-dose injection device. As the two peaks are too close to each other to be possibly attributed to two distinct feedback events, a consolidated peak is defined in-between the two peaks. This may be done by shaping or interpolating a spline function, preferably a cubic spline function, through a selection of points including the two peaks of the double peak, or by another suitable low pass filter. The time of the maximum of the spline function, which coincides with the summit of the consolidated peak, is then retained as the detected peak location or peak center $t_{pm}$ (represented by the vertical dash-dot line). Likewise depicted in FIG. 4 is an evaluation interval 40, or Region-Of-Interest ROI, around the peak maximum location or peak center $t_{pm}$. The evaluation interval 40 has a length D that is less than the length of the data frame, in one embodiment less than half the frame length, and is arranged symmetrically between $t_{pm}-D/2$ and $t_{pm}+D/2$ to both sides of the peak maximum location $t_{pm}$. A typical evaluation interval 40 length D is between 10 and 20 ms, thus extending up to 10 ms to both sides of the peak maximum location $t_{pm}$. If the evaluation interval 40 has a length D that is less than the length of the data frame and in one embodiment is exactly half the data frame length, a single exemplary data frame 41 in which evaluation interval 40 falls can be represented by the dashed arrow 41 with a length twice the width of the evaluation interval 40 in FIG. 4. The single data frame 41 represented would be preceded and followed by data frames of time-adjacent samples.

In the second stage, the origin or source event of the previously detected peak is identified, i.e., the peak is assigned to one of a dial up click, a dial down click, and an expel click event, or possibly discarded as a false positive. This may be done by further processing the first signal data that was exploited to determine the peak location, or on a stream of data frames of parallel, second signal data different from the first signal data and being provided by a second sensor 21a measuring a distinct quantity or aspect of the feedback event. In this case, a peak locator such as a time of peak maximum tpm is taken from the first data and matched to the second signal data as a starting point to delimit or select the data for the following evaluation.

Figure 5:
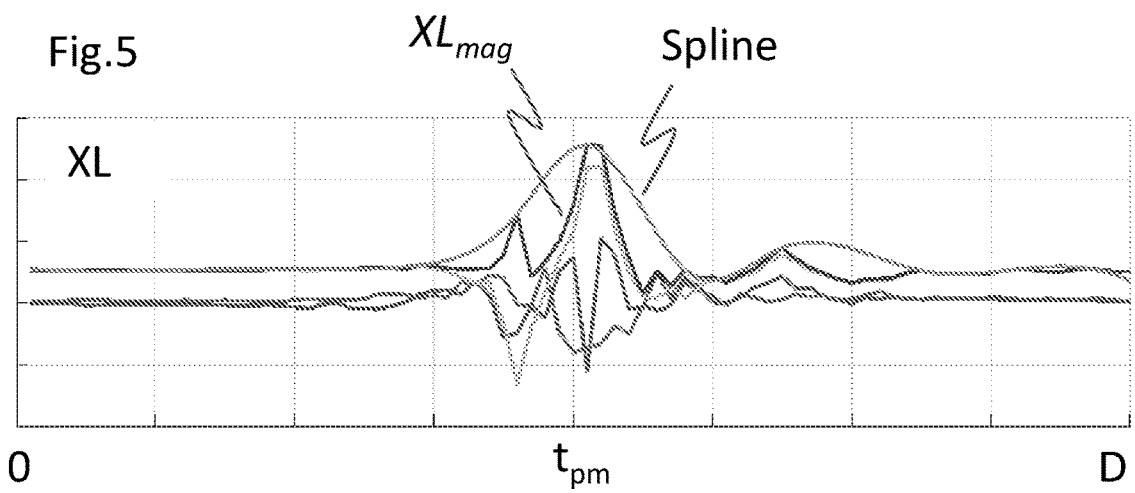
FIG. 5 shows exemplary correlated acceleration and gyroscope signals.
Figure 5:
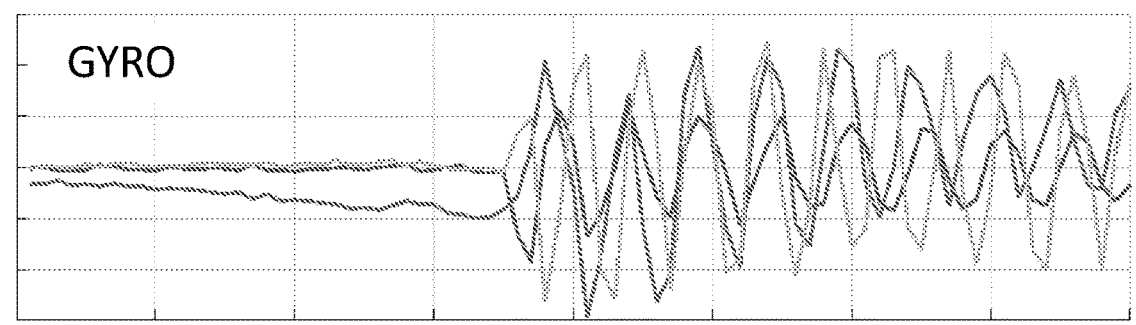

FIG. 5 shows exemplary correlated acceleration (XL, top) and gyroscope (GYRO, bottom) signals of a dial down feedback event over an evaluation interval. In the top graph, in addition to the x, y, z acceleration signals, the acceleration magnitude $XL_{mag}$ is depicted, as well as the interpolating spline function. Per definition, the summit or maximum of the spline function is located at $t_{pm}$ in the center of the evaluation interval depicted. The data most significant for the purpose of peak origin identification is the gyroscope signal of the evaluation interval 40, or Region Of Interest ROI, around the peak maximum location $t_{pm}$.

A suitable algorithm to distinguish and identify the source events is based on a feature analysis. Features are the result of mathematical transformations including spectral analysis, statistical values, or basic mathematical operations. Feature values or instances may be calculated on the signal data of the entire evaluation interval 40, on signal data of a first branch before spline peak maximum, or on signal data of a second branch after spline peak maximum. The contributions of individual branches or of other parts of the evaluation interval, and/or individual single-axis contributions of the three axis may be summed or otherwise aggregated. Exemplary features derived from gyroscope or accelerometer signals, on the signal branch before the peak maximum or after the peak maximum within the evaluation interval, include:

Sum (3-axis) of the GYRO single-axis correlation values of a GYRO test signal with the single axis GYRO signals;
Maximum of the XL magnitude;
Integral of the XL magnitude;
Sum (3-axis) of the XL single-axis sums of absolute derivatives of the single-axis XL signals;
Sum (3-axis) of the GYRO single-axis sums of absolute derivatives of the single-axis GYRO signals;
Sum (3-axis) of the GYRO single-axis integrals of the single-axis GYRO signals.

Figure 6:
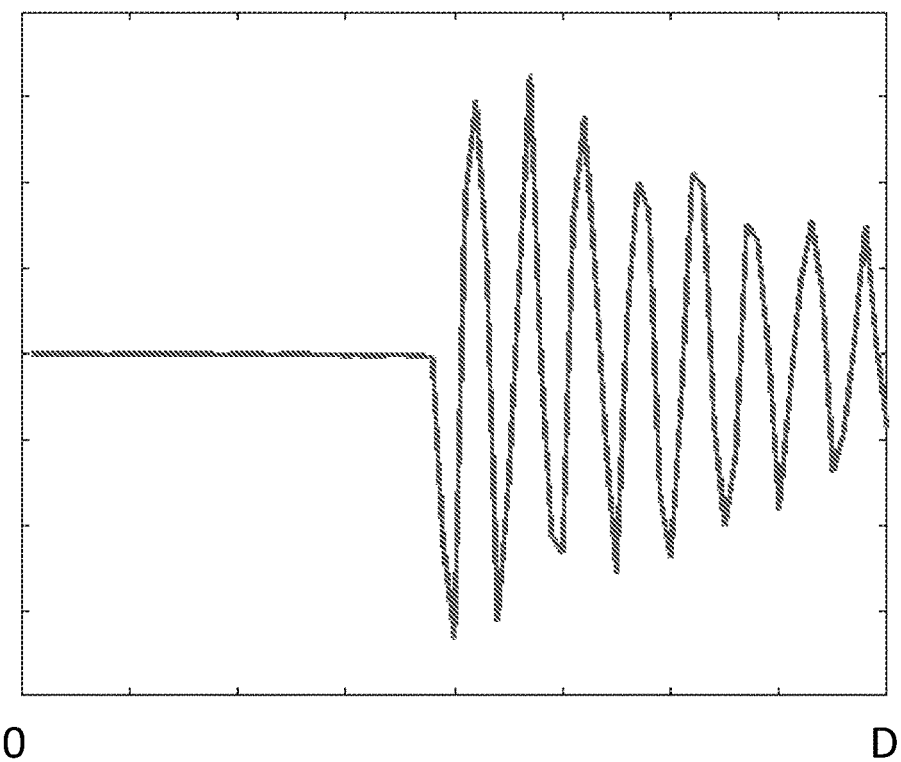
FIG. 6 shows a GYRO test signal of a length equal to an evaluation interval.

FIG. 6 shows an exemplary GYRO test or reference signal of a length D equal to the evaluation interval 40 as used for the derivation of the first-mentioned exemplary feature. The shape of the test signal shown is representative of an expel feedback event, and therefore may be used to positively identify, classify, or assign measured signals emanating from expel feedback events. The test or reference signal may be pre-defined or regularly updated, for instance based on measured signals that have been previously assigned to a particular feedback event. The test signal may be the same for all axes of a multi-axis gyroscope, or be different for different axes.

Figure 7:
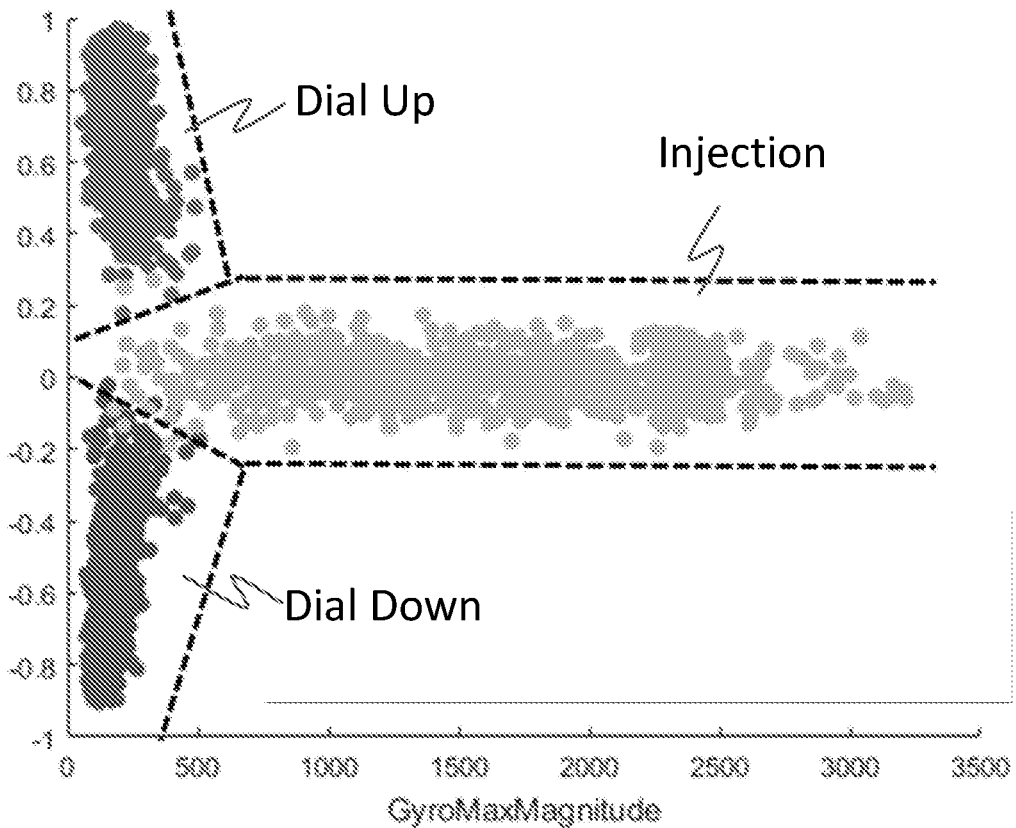
FIG. 7 shows a 2D feature space scatter plot of two exemplary features.

FIG. 7 shows a 2D feature space scatter plot of two exemplary features, i.e., the gyroscope signal maximum magnitude (horizontal axis) and the test signal correlation (vertical axis), wherein each point of the plot represents a feature instance, or a set of feature values, resulting from a feedback event of known origin. The boundaries depicted with straight broken lines are found to quite accurately, but not perfectly, separate the feature instances with distinct origin, and do delimit corresponding areas in the plot denoted as Dial Up, Dial Down, and Injection. Accordingly, the two features are well qualified for the identification of a peak, as any further feature instance derived from the signal resulting from a feedback event with known origin is expected to be located, with a high probability, in the corresponding area of the plot. Higher dimension feature spaces are possible if additional features are retained. Creating a scatter plot of a multi-dimensional feature space allows to assess the ability of a set of features to separate the classes. On such basis, the above two features appear to be well suited, and may therefore be adopted for a training of sophisticated classifiers that supplant the rudimentary or insufficient scatter-plot based identification. Various types of classifiers exist and are based on different concepts but all have the common goal of minimizing the classification error of unknown sample. The best result is obtained by a Support Vector Machine (SVM) with a linear kernel and by a Feed Forward Artificial Neural Network (ANN).

Figure 8:
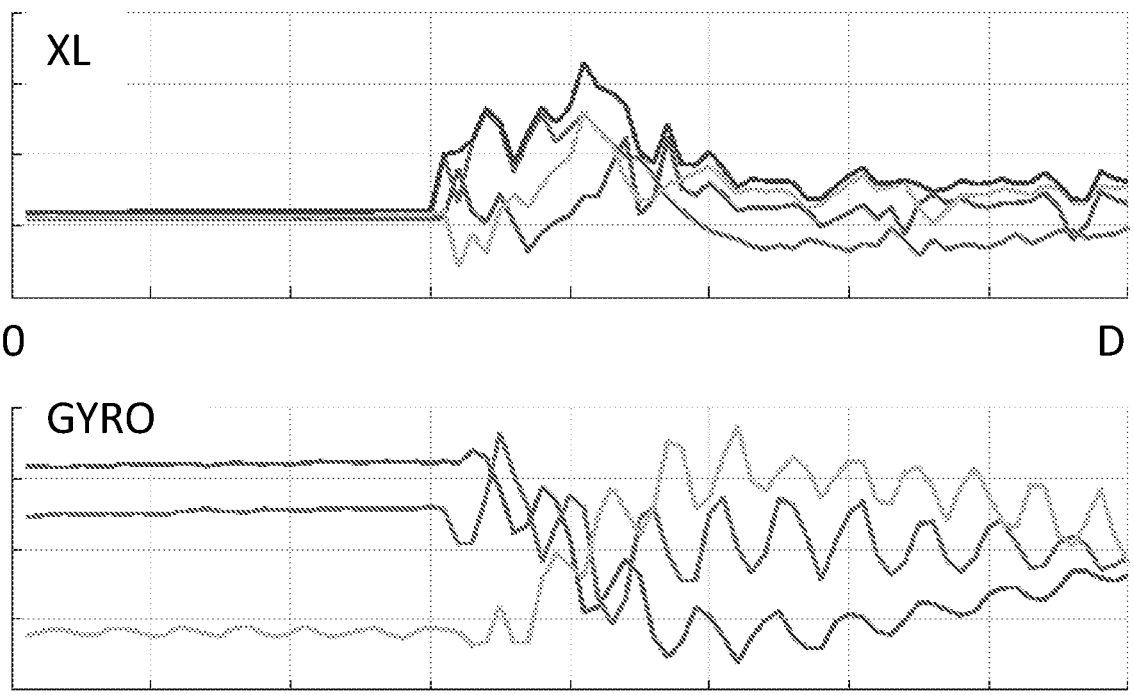
FIG. 8 depicts a false positive pattern in correlated acceleration and gyroscope signals.

FIG. 8 depicts exemplary correlated false positive signals that have to be identified as such in order to avoid, or supplant, an identification as a valid feedback event. False positives result from events other than one of the acknowledged source events, but nevertheless appear to be reasonably assignable to one of the latter. For instance, acceleration peaks on the IMU generated from shocks or by violently shaking the delivery device may result in false positives. To that end, a set of features different from the one adopted for the aforementioned classifier is chosen, and corresponding feature instances or values derived are compared to suitable thresholds or boundary values to identify the peak as a false positive.

FIG. 9 is a block diagram summarizing the steps of an exemplary method of click event identification according to the disclosure. The ultimate plausibility check includes, among others, a comparison of the latest identified source event with one or several immediately preceding identified source event to verify that the identified source events do not change too frequently or present an excessive inter-event delay, or that the number of successive identical events is reasonable. An additional distinction or differentiation of priming signals is made plausible when matching a small expelled or dispensed dose of one or two IUs to a near-vertical orientation (within 10° of the vertical) of the delivery device as determined by the acceleration sensor.

The pre-processing step may include one or several of the steps including sampling or digitizing the raw data signal captured with a feedback sensor 21, 21a to generate a discrete-time signal, analog and/or digital integration of a signal, analog and/or digital filtering of a signal by appropriate high-pass, low-pass, band-pass or notch filters, compressing, equalizing and/or otherwise processing a signal, and storing a discrete-time signal in a data memory. These steps may be performed by appropriate processing means of the feedback sensor itself, or by a dedicated processing unit wired to the sensor.

The electronic components being integrated in the injection device 1 or being part of an electronic module 2 may comprise a visual, audible and/or tactile status indicator indicating to a user a status of the system. The status of the system may include any of a device status of the injection device 1, a module status of the electronic module 2, or a process status of an overall injection process or injection device handling process. The status indicator 25, 25'may be simple and limited to a few Light Emitting Diodes LEDs in traffic-light colors and/or an audible signal generator for generating language-independent beep sounds or simple melodies. The status indicator may explicitly exclude any advanced human-machine interfacing capability, and be limited to a few, specifically less than ten, messages conveyable to the user. In particular, the electronic unit may not be wired to, and the electronic module 2 may be devoid of, a display, screen, or projector for visually transmitting readable instructions, and likewise exclude an artificial speech assistant for reading out loud the instructions. Such advanced HMI functionality including elaborate graphic display and speech output capabilities are preferably being provided by a mobile device communicatively connected to the electronic unit. The status information may be redundant or complementary to primary signals from the injection device that a user may still capture in parallel. In particular, the status information may include a positive confirmation of a dose having been set or corrected, or an indication about a lapse of a minimum holding, delay, or dwell time following completion of a substance expel or piston forwarding activity to inform the user that it is now safe to remove the injection device 1.

A wireless communication unit 23 is connected to the processing unit, and adapted to wirelessly communicate, specifically upload, injection information to a nearby mobile device 3. The injection information includes at least a time stamp and the expelled dose, indicative of a time and quantity of injected medication, and optionally a dialed and/or corrected dose. The injection information may be transmitted instantaneously, or stored in a memory unit 24 connected to the processing unit 23, for later upload or batch transfer. The injection information may, in addition or alternatively, include a quality measure of an injection process, such as a binary flag indicating that a determined dialed dose corresponds to a determined expelled dose.

While the device and method have been described in detail in the drawings and foregoing description, such description is to be considered illustrative or exemplary and not restrictive. Variations to the disclosed embodiments can be understood and effected by those skilled in the art and practicing the disclosure, from a study of the drawings, the disclosure, and the appended claims. In the claims, the word "comprising" does not exclude other elements or steps, and the indefinite article "a" or "an" does not exclude a plurality. The mere fact that certain elements or steps are recited in distinct claims shall not preclude the existence of further meaningful combinations of these elements or steps.

LIST OF REFERENCE NUMBERS 1 injection device
10 device housing
11 dosing sleeve
12 dosing knob
13 discharge button
14 resilient wing/attachment means
2 electronic module
20 module housing
21 first feedback sensor
21a second feedback sensor
22 processing unit
23 transmitter unit
24 data storage unit
25, 25' status indicator
26 printed circuit board
27 battery
3 mobile device
31 patient
32 data server
40 evaluation interval
41 data frame
42 window
44 opening

The invention claimed is:

1. A method of determining a dose of a variable-dose injection device with feedback means generating a number of feedback events proportionate to the dose, comprising:
measuring, by a first feedback sensor, a first signal comprising a first signal peak related to a feedback event, wherein the first feedback sensor is configured as a multi-axis gyroscope;
detecting the first signal peak in the first signal;
selecting an evaluation interval comprising the detected first signal peak;
deriving, from the first signal limited to the evaluation interval, a feature of the feedback event, wherein deriving the feature comprises:
calculating, for each axis of the gyroscope, a correlation value of a test signal with a single-axis gyroscope signal, and adding the correlation values; or
calculating, for each axis of the gyroscope, a sum of absolute derivatives of a single-axis gyroscope signal, and adding the sums;

identifying, from the derived feature, the feedback event as an expel feedback event; and counting the number of identified expel feedback events to determine an expelled dose.

2. The method of claim 1, further comprising identifying, from the derived feature, the feedback event as one of a dial up or dial down feedback event; and counting a number of identified dial up and dial down feedback events to determine a dialed dose.

3. The method of claim 1, further comprising:

defining, in a measured signal, successive data frames of pre-defined length;

prepending signal data of a selected evaluation interval in a first data frame to a second data frame if the selected evaluation interval extends into the second data frame; and processing the signal data of the selected evaluation interval within the second data frame.

4. The method claim 3, further comprising:

deriving, from the evaluation interval, a non-event feature; and identifying, from the derived non-event feature, the first signal as comprising a false positive.

5. An electronic module for a variable dose delivery device comprising:

a first feedback sensor configured as a multi-axis gyroscope and adapted to measure a first signal comprising a first signal peak related to a feedback event generated by a feedback means of the variable dose delivery device; and a signal processing unit configured to:

detect, using data from the first feedback sensor, the first signal peak in the first signal;

select an evaluation interval from a portion of the first signal, the evaluation interval comprising the detected peak;

derive, from the evaluation interval, a feature of the feedback event using data from the first feedback sensor, wherein deriving the feature comprises:

calculating, for each axis of the gyroscope. a correlation value of a test signal with a single-axis gyroscope signal, and adding the correlation values; or calculating, for each axis of the gyroscope, a sum of absolute derivatives of a single-axis gyroscope signal, and adding the sums; and identify, from the derived feature, the feedback event as one of a dial up, dial down, or expel feedback event.

6. The electronic module of claim 5, further comprising attachment means for releasable attachment of the electronic module to a housing of the variable dose delivery device.

7. The electronic module of claim 5, further comprising a board with a printed circuit and a battery with a main surface arranged parallel to the board, wherein the battery is accommodated in a recess of the board and extends to both sides of the board.

8. The electronic module of claim 5, further comprising a module housing with an opening allowing a user to read a dose dialed and depicted in a window of the delivery device, wherein a border of the opening is illuminated.

9. The electronic module of claim 5, wherein the signal processing unit is configured to evaluate a signal measured independent of a dose setting or a dose expel process of the delivery device to detect a device handling activity of a user.

10. The electronic module of claim 9, wherein the signal processing unit is configured to track, from the evaluated signal and during an expel process, a position of the delivery device, and to acknowledge the expel process as an injection process if the tracked position is between two co-centric spherical surfaces distant less than a penetration depth of the delivery device.

11. The electronic module of claim 5, wherein the first feedback sensor is adapted to measure the first signal at a sampling rate of no more than 10 KHz; and the processing unit is configured to process the measured first signal in data frames of a length of at least 2 ms, and to select an evaluation interval of a length D of no more than the length of a data frame.

12. An electronic module for a variable dose delivery device comprising:

a first feedback sensor configured as a multi-axis gyroscope and adapted to measure a first signal comprising a first signal peak related to a feedback event and generated with the variable dose delivery device; and a signal processing unit configured to:

receive a plurality of data frames sampled from the first signal;

detect the first signal peak in a data frame sampled from the first signal;

select, using data from the first feedback sensor, an evaluation interval from a portion of the first signal, the evaluation interval comprising the detected peak;

derive, from the evaluation interval, a feature of the feedback event using data from the first feedback sensor-a second feedback sensor, wherein deriving the feature comprises:

calculating, for each axis of the gyroscope, a correlation value of a test signal with a single-axis gyroscope signal, and adding the correlation values; or calculating, for each axis of the gyroscope, a sum of absolute derivatives of a single-axis gyroscope signal, and adding the sums; and identify, from the derived feature, the feedback event as one of a dose dial up, dose dial down, or dose expel feedback event.

13. The electronic module of claim 12, further comprising a second feedback sensor adapted to measure a second signal comprising a second signal peak related to the feedback event, wherein the signal processing unit is further configured to receive a plurality of data frames sampled from the second signal, detect the second signal peak in a data frame sampled from the second signal and process the second signal peak to derive and identify a feedback event by a same set of evaluation steps as for the first signal peak.

14. The electronic module of claim 13, wherein the signal processing unit is further configured to:

derive, from the evaluation interval of the first signal or the second signal, a non-event feature; and identify, from the derived non-event feature, the first signal or second signal as a false positive.

* * * * *